(12) United States Patent
Goto et al.

(10) Patent No.: US 9,233,900 B2
(45) Date of Patent: Jan. 12, 2016

(54) METHOD FOR PRODUCING GLYCOLS FROM OXIRANE COMPOUND

(71) Applicant: Sumitomo Chemical Company Limited, Tokyo (JP)

(72) Inventors: Shigeru Goto, Tokyo (JP); Kenji Itoh, Chiba (JP); Koji Shinohara, Chiba (JP); Masayuki Yoshii, Chiba (JP); Shinjiro Ishihara, Ehime (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/399,567

(22) PCT Filed: May 10, 2013

(86) PCT No.: PCT/JP2013/063732
§ 371 (c)(1),
(2) Date: Nov. 7, 2014

(87) PCT Pub. No.: WO2013/168827
PCT Pub. Date: Nov. 14, 2013

(65) Prior Publication Data
US 2015/0133697 A1 May 14, 2015

(30) Foreign Application Priority Data
May 11, 2012 (JP) .................................. 2012-109221

(51) Int. Cl.
| | |
|---|---|
| *C07C 41/02* | (2006.01) |
| *C07C 29/80* | (2006.01) |
| *C07C 41/42* | (2006.01) |
| *C07C 41/03* | (2006.01) |
| *C07C 29/10* | (2006.01) |

(52) U.S. Cl.
CPC .............. *C07C 41/02* (2013.01); *C07C 29/106* (2013.01); *C07C 29/80* (2013.01); *C07C 41/03* (2013.01); *C07C 41/42* (2013.01)

(58) Field of Classification Search
CPC ...................................................... C07C 41/02
See application file for complete search history.

(56) References Cited

U.S. PATENT DOCUMENTS

| | | | |
|---|---|---|---|
| 4,937,393 A | 6/1990 | Masuda et al. | |
| 6,211,419 B1 | 4/2001 | Strickler et al. | |
| 6,448,456 B1 | 9/2002 | Strickler et al. | |
| 2009/0187049 A1* | 7/2009 | Li et al. .......................... | 568/678 |
| 2010/0063327 A1* | 3/2010 | Hoy et al. ...................... | 568/613 |

FOREIGN PATENT DOCUMENTS

| | | |
|---|---|---|
| JP | 62-116530 A | 5/1987 |
| JP | 2003-531878 A | 5/1987 |
| JP | 62-126144 A | 6/1987 |
| JP | 62-126145 A | 6/1987 |
| JP | 2004-528390 A | 9/2004 |
| JP | 2013-082672 A | 5/2013 |

OTHER PUBLICATIONS

Martin, et al., Glycols, Propylene Glycols. (2000) Kirk-Othmer Encyclopedia of Chemical Technology, p. 1-10.
International Search Report issued Aug. 20, 2013 in PCT/JP2013/063732.
International Written Opinion issued Aug. 20, 2013 in PCT/JP2013/063732.
IPRP issued May 10, 2013 in PCT/JP2013/063732.
Office Action issued Jul. 2, 2015 in corresponding CN App No. 201380024242.8.

* cited by examiner

*Primary Examiner* — Brian J Davis
(74) *Attorney, Agent, or Firm* — Panitch Schwarze Belisario & Nadel LLP

(57) ABSTRACT

There is provided a method for producing dipropylene glycol (DPG) and/or tripropylene glycol (TPG) including: (A) reacting a raw material liquid including propylene oxide and water to obtain a reaction liquid including unreacted water, propylene glycol (PG), DPG and/or TPG, and an alcohol compound excluding PG, DPG, and TPG; (B) separating, from the reaction liquid, a first liquid containing water and the alcohol compound and a second liquid containing the PG, DPG and/or TPG and optionally the alcohol compound; (C) removing a part of the alcohol compound from the first liquid to obtain a third liquid containing water and optionally a part of the alcohol compound; (D) separating, from the second liquid, a fourth liquid containing the PG and optionally the alcohol compound, and a fifth liquid containing the DPG and/or TPG and optionally the alcohol compound; and (E) recycling a part of the third liquid to step (A).

10 Claims, 2 Drawing Sheets

Prior Art

Prior Art

US 9,233,900 B2

METHOD FOR PRODUCING GLYCOLS FROM OXIRANE COMPOUND

CROSS-REFERENCE TO RELATED APPLICATION

This application is a Section 371 of International Application No. PCT/JP2013/063732, filed May 10, 2013, which was published in the Japanese language on Nov. 14, 2013, under International Publication No. WO 2013/168827 A1, and the disclosure of which is incorporated herein by reference.

TECHNICAL FIELD

The present invention relates to a method for producing dipropylene glycol and/or tripropylene glycol with high selectivity from propylene oxide and water.

BACKGROUND ART

Dipropylene glycol is a compound used for a raw material for polyester resin or polyurethane resin, a raw material for acrylic esters, a hydraulic fluid, an antifreezing liquid, a wetting agent for cellophane, an oil-water compatibilizer, a solvent for printing ink, a raw material for cosmetics, a solvent for flavorants, toiletry solvents, etc. and tripropylene glycol is a compound used for a raw material for polyester resin or polyurethane resin, a raw material for acrylic esters, a solvent for water-soluble oils, a solvent for ink, etc. Dipropylene glycol and tripropylene glycol are known to be produced successfully as a by-product in the production of propylene glycol from propylene oxide and water; for example, Non-Patent Document 1 discloses that dipropylene glycol and tripropylene glycol are formed as by-products in producing propylene glycol by reacting propylene oxide with water and also discloses a step of removing excess water after the reaction.

PRIOR ART DOCUMENTS

Non-Patent Document

Non-Patent Document 1: Martin, A. E. and Murphy, F. H. 2000. Glycols, Propylene Glycols. Kirk-Othmer Encyclopedia of Chemical Technology.

SUMMARY OF THE INVENTION

Problems to be Solved by the Invention

The production method disclosed in Non-Patent Document 1, however, fails to disclose details of by-products. Accordingly, there is a need for methods for producing dipropylene glycol and/or tripropylene glycol industrially with high selectivity by controlling by-product concentration.

It is an object of the present invention to provide a method for producing dipropylene glycol and/or tripropylene glycol with high selectivity from propylene oxide and water by controlling by-product concentration.

Means for Solving the Problems

First, the present invention relates to a method for producing dipropylene glycol and/or tripropylene glycol, the method comprising steps (A), (B), (C), (D), and (E) defined below, step (A): the step of reacting a raw material liquid comprising propylene oxide and water to obtain a reaction liquid comprising unreacted water, propylene glycol, dipropylene glycol and/or tripropylene glycol, and an alcohol compound excluding propylene glycol, dipropylene glycol, and tripropylene glycol, step (B): the step of separating, from the reaction liquid, a first liquid comprising the water and the alcohol compound each contained in the reaction liquid, and a second liquid comprising the propylene glycol and the dipropylene glycol and/or tripropylene glycol each contained in the reaction liquid and optionally comprising the alcohol compound contained in the reaction liquid, step (C): the step of removing at least a part of the alcohol compound contained in the first liquid from the first liquid to obtain a third liquid comprising the water contained in the first liquid and optionally comprising a part of the alcohol compound contained in the first liquid, step (D): the step of separating, from the second liquid, a fourth liquid comprising the propylene glycol contained in the second liquid and optionally comprising the alcohol compound contained in the second liquid, and a fifth liquid comprising the dipropylene glycol and/or tripropylene glycol contained in the second liquid and optionally comprising the alcohol compound contained in the second liquid, step (E): the step of recycling at least a part of the third liquid to step (A) as a component of the raw material liquid.

Second, the present invention relates to a method for producing dipropylene glycol and/or tripropylene glycol, the method comprising steps (I), (J), (K), and (L) defined below, step (I): the step of reacting a raw material liquid comprising propylene oxide and water to obtain a reaction liquid comprising unreacted water, propylene glycol, dipropylene glycol and/or tripropylene glycol, and an alcohol compound excluding propylene glycol, dipropylene glycol, and tripropylene glycol, step (J): the step of separating, from the reaction liquid, a seventh liquid comprising the water, the alcohol compound, and the propylene glycol each contained in the reaction liquid, and an eighth liquid comprising the dipropylene glycol and/or tripropylene glycol contained in the reaction liquid and optionally comprising the alcohol compound contained in the reaction liquid, step (K): the step of removing at least a part of the alcohol compound contained in the seventh liquid from the seventh liquid to obtain a ninth liquid comprising the propylene glycol contained in the seventh liquid, optionally comprising the whole or apart of the water contained in the seventh liquid, and optionally comprising a part of the alcohol compound contained in the seventh liquid, step (L): the step of recycling at least a part of the ninth liquid to step (I) as a component of the raw material liquid.

Third, the present invention relates to a method for producing dipropylene glycol and/or tripropylene glycol, the method comprising steps (M), (N), (O), and (P) defined below, step (M): the step of reacting a raw material liquid comprising propylene oxide and water to obtain a reaction liquid comprising propylene glycol, dipropylene glycol and/or tripropylene glycol, and an alcohol compound excluding propylene glycol, dipropylene glycol, and tripropylene glycol, and optionally comprising unreacted water, step (N): the step of removing at least a part of the alcohol compound contained in the reaction liquid from the reaction liquid to obtain a tenth liquid comprising the propylene glycol and the dipropylene glycol and/or tripropylene glycol each contained in the reaction liquid and optionally comprising the water and/or apart of the alcohol compound each contained in the reaction liquid, step (O): the step of separating, from the tenth liquid, an eleventh liquid comprising the propylene glycol contained in the tenth liquid and optionally comprising the water and/or the alcohol compound each contained in the tenth liquid, and a twelfth liquid comprising the dipropylene glycol and/or tripropylene glycol contained in the tenth liquid and optionally comprising the alcohol compound contained in the tenth liquid, step (P): the step of recycling at least a part of the eleventh liquid to step (M) as a component of the raw material liquid.

Effect of the Invention

According to the present invention, dipropylene glycol and/or tripropylene glycol can be produced with high selectivity from propylene oxide and water.

MODE FOR CARRYING OUT THE INVENTION

Figure 1:
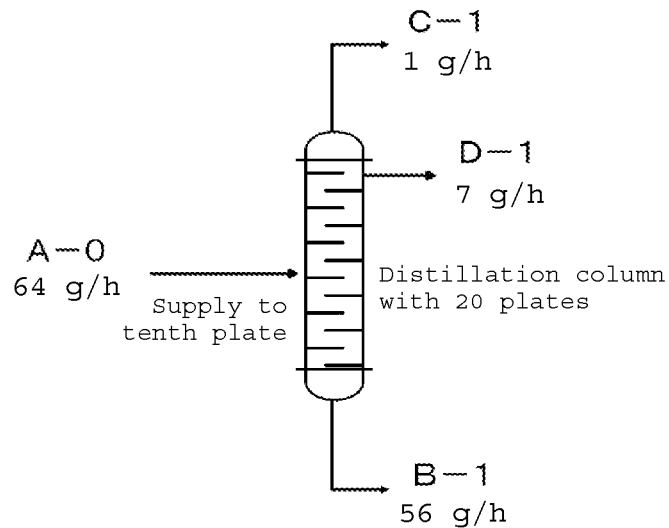
FIG. 1 is a diagram illustrating steps (B) and (C) of Example 1.

The first method of the present invention for producing dipropylene glycol and/or tripropylene glycol comprises steps (A), (B), (C), (D), and (E) defined below, step (A): the step of reacting a raw material liquid comprising propylene oxide and water to obtain a reaction liquid comprising unreacted water, propylene glycol, dipropylene glycol and/or tripropylene glycol, and an alcohol compound excluding propylene glycol, dipropylene glycol, and tripropylene glycol, step (B): the step of separating, from the reaction liquid, a first liquid comprising the water and the alcohol compound each contained in the reaction liquid, and a second liquid comprising the propylene glycol and the dipropylene glycol and/or tripropylene glycol each contained in the reaction liquid and optionally comprising the alcohol compound contained in the reaction liquid, step (C): the step of removing at least a part of the alcohol compound contained in the first liquid from the first liquid to obtain a third liquid comprising the water contained in the first liquid and optionally comprising a part of the alcohol compound contained in the first liquid, step (D): the step of separating, from the second liquid, a fourth liquid comprising the propylene glycol contained in the second liquid and optionally comprising the alcohol compound contained in the second liquid, and a fifth liquid comprising the dipropylene glycol and/or tripropylene glycol contained in the second liquid and optionally comprising the alcohol compound contained in the second liquid, step (E): the step of recycling at least a part of the third liquid to step (A) as a component of the raw material liquid.

Step (A) is the step of reacting a raw material liquid comprising propylene oxide and water to obtain a reaction liquid comprising unreacted water, propylene glycol, dipropylene glycol and/or tripropylene glycol, and an alcohol compound excluding propylene glycol, dipropylene glycol, and tripropylene glycol.

In step (A), the propylene oxide and the water in the raw material liquid are consumed and dipropylene glycol and/or tripropylene glycol and an alcohol compound are generated. When the raw material liquid contains no propylene glycol, propylene glycol is generated in the reaction of step (A), whereas when the raw material liquid contains propylene glycol, propylene glycol is or is not generated in the reaction of step (A). In one embodiment, the raw material liquid comprises propylene glycol.

In step (A), the propylene oxide may be propylene oxide produced by any production method, and there can be used propylene oxide produced by dehydrochlorinating, with a basic compound, a mixture produced by making propylene react with an aqueous solution of chlorine, propylene oxide produced by making propylene react in the presence of a catalyst with ethylbenzene hydroperoxide produced by oxidizing ethylbenzene, propylene oxide produced by making propylene react in the presence of a catalyst with isopropylbenzene hydroperoxide produced by oxidizing isopropylbenzene, propylene oxide produced by making propylene react in the presence of a catalyst with tert-butyl hydroperoxide produced by oxidizing isobutane, and propylene oxide produced by making propylene react in the presence of a catalyst with hydrogen peroxide.

In step (A), distilled water, pure water, ion-exchanged water, steam condensate, etc. can be used as the water.

In step (A), the reaction is preferably performed in the presence of a catalyst in terms of improvement in selectivity. The catalyst to be used is not particularly restricted, and examples thereof include alkali metal hydroxides, such as lithium hydroxide, sodium hydroxide, potassium hydroxide, rubidium hydroxide, and cesium hydroxide, inorganic acids, such as hydrochloric acid, sulfuric acid, and phosphoric acid, ion exchange resin, zeolite, silica-alumina, amine compounds, and catalysts containing at least one element selected from the group consisting of vanadium, niobium, and tantalum. Among these catalysts, alkali metal hydroxides, such as lithium hydroxide, sodium hydroxide, potassium hydroxide, rubidium hydroxide, and cesium hydroxide, or catalysts containing at least one element selected from the group consisting of vanadium, niobium, and tantalum are preferable from the viewpoint of being high in selectivity to dipropylene glycol and/or tripropylene glycol. Examples of the catalysts containing at least one element selected from the group consisting of vanadium, niobium, and tantalum include vanadium pentoxide, vanadium dioxide, vanadium trioxide, niobium pentoxide, niobium dioxide, niobium monoxide, tantalum pentoxide, vanadic acid, niobic acid, and tantalic acid.

Such catalysts containing at least one element selected from the group consisting of vanadium, niobium, and tantalum may be used individually or in combination.

Such catalysts containing at least one element selected from the group consisting of vanadium, niobium, and tantalum may be used while having been mixed physically with a substantially inert solid. Examples of such a substantially inert solid include silica, alumina, titania, zirconia, ceria, activated carbon, graphite, magnesia, and calcia.

Examples of the reaction system of step (A) include a batch system using a tank reactor, a semi-continuous or continuous slurry method, and a continuous fixed bed method using a tubular reactor. As the tank reactor, a single-stage or multi-stage mixing tank is usually used. Examples of the tubular reactor include fixed bed reactors comprising a single unit or a plurality of units arranged in series, the unit or each of the units having a single tube or having a multitubular heat exchange structure having many tubes arranged in parallel.

The reaction temperature of step (A) is preferably 30 to 350° C., more preferably 50 to 300° C.

The reaction pressure applied when step (A) is carried out in a reactor, which may be any pressure under which the liquid within the reactor is in a liquid phase, is preferably normal pressure to 50 MPa-G, and more preferably 0.1 to 20 MPa-G.

In step (A), the amount of the water relative to the propylene oxide in the raw material liquid is preferably 0.05 to 100 mol, more preferably 0.1 to 50 mol, and even more preferably 0.2 to 10 mol per mol of propylene oxide.

Preferably, the raw material liquid in step (A) contains propylene glycol.

Step (B) is the step of separating, from the reaction liquid, a first liquid comprising the water and the alcohol compound each contained in the reaction liquid, and a second liquid comprising the propylene glycol and the dipropylene glycol and/or tripropylene glycol each contained in the reaction liquid and optionally comprising the alcohol compound contained in the reaction liquid.

The method of performing the separation of step (B) may be any method by which the reaction liquid can be separated into the first liquid and the second liquid, a method involving distillation is preferable in terms of ease of operation and separability.

When distillation is used as the method of performing the separation of step (B), distillation conditions are not particularly limited; the temperature within a distillation column is 0 to 300° C., preferably 10 to 250° C., the pressure within the distillation column is −0.1 to 10 MPa-G, preferably −0.09 to 5 MPa-G, and the number of plates of the distillation column is 1 to 100, preferably 10 to 50.

Step (C) is the step of removing at least a part of the alcohol compound contained in the first liquid from the first liquid to obtain a third liquid comprising the water contained in the first liquid and optionally comprising a part of the alcohol compound contained in the first liquid.

Step (C) may be performed by any method as long as at least a part of the alcohol compound can be removed from the first liquid and step (C) can be practiced by partial condensation, distillation, extraction, adsorption, reaction, etc. In terms of ease of operation and separability, a method by partial condensation or distillation is preferred.

When distillation is used as the method of removing at least a part of the alcohol compound of step (C), distillation conditions are not particularly limited; the temperature within a distillation column is 0 to 300° C., preferably 10 to 250° C., the pressure within the distillation column is −0.1 to 10 MPa-G, preferably −0.09 to 5 MPa-G, and the number of plates of the distillation column is 1 to 100, preferably 10 to 50.

As to step (C), the alcohol compound is preferably removed so that the concentration of the alcohol compound in total in the raw material liquid comprising propylene oxide and water for step (A) may become 2000 mmol/kg or less when the liquid obtained in step (C) has been recycled by step (E) described below as a component of the raw material liquid in step (A). The concentration of the alcohol compound in total in the raw material liquid for step (A) is more preferably 1000 mmol/kg or less, more preferably 400 mmol/kg or less, and most preferably 200 mmol/kg or less. If the concentration of the alcohol compound is 2000 mmol/kg or less, the selectivity to dipropylene glycol and/or tripropylene glycol improves more.

Examples of the alcohol compound to be removed in the present invention include methanol, ethanol, 1-propanol, 2-propanol, 1-butanol, 2-butanol, 2-methyl-1-propanol, 2-methyl-2-propanol, 1-pentanol, 3-methyl-1-butanol, 2,2-dimethyl-1-propanol, cyclopentanol, 1-hexanol, cyclohexanol, allyl alcohol, propylene glycol monopropyl ether, dipropylene glycol monopropyl ether, propylene glycol monoallyl ether, dipropylene glycol monoallyl ether, and hydroxyacetone; since especially allyl alcohol, 1-propanol, or 2-propanol will cause decrease in selectivity to dipropylene glycol and/or tripropylene glycol, allyl alcohol, 1-propanol, or 2-propanol is preferably removed.

Step (D) is the step of separating, from the second liquid, a fourth liquid comprising the propylene glycol contained in the second liquid and optionally comprising the alcohol compound contained in the second liquid, and a fifth liquid comprising the dipropylene glycol and/or tripropylene glycol contained in the second liquid and optionally comprising the alcohol compound contained in the second liquid.

The method of performing the separation of step (D) may be any method by which the second liquid can be separated into the fourth liquid and the fifth liquid, a method involving distillation is preferable in terms of ease of operation and separability.

When distillation is used as the method of performing the separation of step (D), distillation conditions are not particularly limited; the temperature within a distillation column is 0 to 300° C., preferably 10 to 250° C., the pressure within the distillation column is −0.1 to 5 MPa-G, preferably −0.09 to 1 MPa-G, and the number of plates of the distillation column is 1 to 100, preferably 10 to 50.

In the present invention, the step of separating dipropylene glycol and/or tripropylene glycol from the fifth liquid obtained in the step (D) (hereafter described as "purification step (1)") may be provided.

The method of performing the separation of purification step (1), which may be any method as long as it is a method by which dipropylene glycol and/or tripropylene glycol can be separated from the fifth liquid, is preferably a method using distillation in terms of ease of operation and separability.

In purification step (1), dipropylene glycol and/or tripropylene glycol may be separated from the fifth liquid in one step, or alternatively tripropylene glycol may be separated after dipropylene glycol is separated.

When distillation is used as the method of performing the separation of purification step (1), distillation conditions are not particularly limited; the temperature within a distillation column is 0 to 300° C., preferably 10 to 250° C., the pressure within the distillation column is −0.1 to 1 MPa-G, preferably −0.09 to 0.1 MPa-G, and the number of plates of the distillation column is 1 to 100, preferably 10 to 50.

Step (E) is the step of recycling at least a part of the third liquid to step (A) as a component of the raw material liquid.

In the present invention, when unreacted propylene oxide is present in the reaction liquid obtained in the step (A), the unreacted propylene oxide may be collected and then reused by being recycled to step (A) as a component of the raw material liquid. The method of collecting the unreacted propylene oxide, which may be any method as long as it is a method by which the unreacted propylene oxide can be collected from the reaction liquid, is preferably a method using distillation from the viewpoint of ease of operation or separability.

When distillation is used as the method of collecting unreacted propylene oxide, distillation conditions are not particularly limited; the temperature within a distillation column is 0 to 300° C., preferably 10 to 250° C., the pressure within the distillation column is −0.1 to 20 MPa-G, preferably −0.09 to 10 MPa-G, and the number of plates of the distillation column is 1 to 100, preferably 10 to 50.

In the present invention, there may be further done step (F) of recycling at least a part of the fourth liquid obtained in the step (D) to step (A) as a component of the raw material liquid. The at least a part of the fourth liquid may be mixed with the components of the raw material liquid of step (A), etc., and then supplied to a reactor, or alternatively it may be supplied separately from the components of the raw material liquid of step (A), etc.

In the present invention, it is also permitted to further perform step (G) of removing at least a part of the alcohol compound contained in the fourth liquid from the fourth liquid to obtain a sixth liquid containing the propylene glycol contained in the fourth liquid and optionally containing a part of the alcohol compound contained in the fourth liquid, and step (H) of recycling at least a part of the sixth liquid to step (A) as a component of the raw material liquid. The at least a part of the sixth liquid may be mixed with the components of the raw material liquid of step (A), etc., and then supplied to a reactor, or alternatively it may be supplied separately from the components of the raw material liquid of step (A), etc.

Step (G) may be performed by any method as long as at least a part of the alcohol compound can be removed from the fourth liquid obtained in the step (D) and step (G) can be practiced by partial condensation, distillation, extraction, adsorption, reaction, etc. In terms of ease of operation and separability, a method by partial condensation or distillation is preferred.

When distillation is used as the method of removing at least a part of the alcohol compound of step (G), distillation conditions are not particularly limited; the temperature within a distillation column is 0 to 300° C., preferably 10 to 250° C., the pressure within the distillation column is −0.1 to 10 MPa-G, preferably −0.09 to 5 MPa-G, and the number of plates of the distillation column is 1 to 100, preferably 10 to 50.

The second method of the present invention for producing dipropylene glycol and/or tripropylene glycol comprises steps (I), (J), (K), and (L) defined below.

A method for producing dipropylene glycol and/or tripropylene glycol, the method comprising steps (I), (J), (K), and (L) defined below, step (I): the step of reacting a raw material liquid comprising propylene oxide and water to obtain a reaction liquid comprising unreacted water, propylene glycol, dipropylene glycol and/or tripropylene glycol, and an alcohol compound excluding propylene glycol, dipropylene glycol, and tripropylene glycol, step (J): the step of separating, from the reaction liquid, a seventh liquid comprising the water, the alcohol compound, and the propylene glycol each contained in the reaction liquid, and an eighth liquid comprising the dipropylene glycol and/or tripropylene glycol contained in the reaction liquid and optionally comprising the alcohol compound contained in the reaction liquid, step (K): the step of removing at least a part of the alcohol compound contained in the seventh liquid from the seventh liquid to obtain a ninth liquid comprising the propylene glycol contained in the seventh liquid, optionally comprising the whole or a part of the water contained in the seventh liquid, and optionally comprising a part of the alcohol compound contained in the seventh liquid, step (L): the step of recycling at least a part of the ninth liquid to step (I) as a component of the raw material liquid.

Step (I) is the step of reacting a raw material liquid comprising propylene oxide and water to obtain a reaction liquid comprising unreacted water, propylene glycol, dipropylene glycol and/or tripropylene glycol, and an alcohol compound excluding propylene glycol, dipropylene glycol, and tripropylene glycol.

In step (I), the propylene oxide and the water in the raw material liquid are consumed and dipropylene glycol and/or tripropylene glycol and an alcohol compound are generated. When the raw material liquid contains no propylene glycol, propylene glycol is generated in the reaction of step (I), whereas when the raw material liquid contains propylene glycol, propylene glycol is or is not generated in the reaction of step (I). In one embodiment, the raw material liquid comprises propylene glycol.

In step (I), the propylene oxide may be propylene oxide produced by any production method, and there can be used propylene oxide produced by dehydrochlorinating, with a basic compound, a mixture produced by making propylene react with an aqueous solution of chlorine, propylene oxide produced by making propylene react in the presence of a catalyst with ethylbenzene hydroperoxide produced by oxidizing ethylbenzene, propylene oxide produced by making propylene react in the presence of a catalyst with isopropylbenzene hydroperoxide produced by oxidizing isopropylbenzene, propylene oxide produced by making propylene react in the presence of a catalyst with tert-butyl hydroperoxide produced by oxidizing isobutane, and propylene oxide produced by making propylene react in the presence of a catalyst with hydrogen peroxide.

In step (I), distilled water, pure water, ion-exchanged water, steam condensate, etc. can be used as the water.

In step (I), the reaction is preferably performed in the presence of a catalyst in terms of improvement in selectivity. The catalyst to be used is not particularly restricted, and examples thereof include alkali metal hydroxides, such as lithium hydroxide, sodium hydroxide, potassium hydroxide, rubidium hydroxide, and cesium hydroxide, inorganic acids, such as hydrochloric acid, sulfuric acid, and phosphoric acid, ion exchange resin, zeolite, silica-alumina, amine compounds, and catalysts containing at least one element selected from the group consisting of vanadium, niobium, and tantalum. Among these catalysts, alkali metal hydroxides, such as lithium hydroxide, sodium hydroxide, potassium hydroxide, rubidium hydroxide, and cesium hydroxide, or catalysts containing at least one element selected from the group consisting of vanadium, niobium, and tantalum are preferable from the viewpoint of being high in selectivity to dipropylene glycol and/or tripropylene glycol. Examples of the catalysts containing at least one element selected from the group consisting of vanadium, niobium, and tantalum include vanadium pentoxide, vanadium dioxide, vanadium trioxide, niobium pentoxide, niobium dioxide, niobium monoxide, tantalum pentoxide, vanadic acid, niobic acid, and tantalic acid.

Such catalysts containing at least one element selected from the group consisting of vanadium, niobium, and tantalum may be used individually or in combination.

Such catalysts containing at least one element selected from the group consisting of vanadium, niobium, and tantalum may be used while having been mixed physically with a substantially inert solid. Examples of such a substantially inert solid include silica, alumina, titania, zirconia, ceria, activated carbon, graphite, magnesia, and calcia.

Examples of the reaction system of step (I) include a batch system using a tank reactor, a semi-continuous or continuous slurry method, and a continuous fixed bed method using a tubular reactor. As the tank reactor, a single-stage or multi-stage mixing tank is usually used. Examples of the tubular reactor include fixed bed reactors comprising a single unit or a plurality of units arranged in series, the unit or each of the units having a single tube or having a multitubular heat exchange structure having many tubes arranged in parallel.

The reaction temperature of step (I) is preferably 30 to 350° C., more preferably 50 to 300° C.

The reaction pressure applied when step (I) is carried out in a reactor, which may be any pressure under which the liquid within the reactor is in a liquid phase, is preferably normal pressure to 50 MPa-G, and more preferably 0.1 to 20 MPa-G.

In step (I), the amount of the water relative to the propylene oxide in the raw material liquid is preferably 0.05 to 100 mol, more preferably 0.1 to 50 mol, and even more preferably 0.2 to 10 mol per mol of propylene oxide.

Preferably, the raw material liquid in step (I) contains propylene glycol.

Step (J) is the step of separating, from the reaction liquid, a seventh liquid comprising the water, the alcohol compound, and the propylene glycol each contained in the reaction liquid, and an eighth liquid comprising the dipropylene glycol and/or tripropylene glycol contained in the reaction liquid and optionally comprising the alcohol compound contained in the reaction liquid.

The method of performing the separation of step (J) may be any method by which the reaction liquid can be separated into the seventh liquid and the eighth liquid, a method involving distillation is preferable in terms of ease of operation and separability.

When distillation is used as the method of performing the separation of step (J), distillation conditions are not particularly limited; the temperature within a distillation column is 0 to 300° C., preferably 10 to 250° C., the pressure within the distillation column is −0.1 to 5 MPa-G, preferably −0.09 to 1 MPa-G, and the number of plates of the distillation column is 1 to 100, preferably 10 to 50.

In the present invention, the step of separating dipropylene glycol and/or tripropylene glycol from the eighth liquid obtained in the step (J) (hereafter described as "purification step (2)") may be provided.

The method of performing the separation of purification step (2), which may be any method as long as it is a method by which dipropylene glycol and/or tripropylene glycol can be separated from the eighth liquid, is preferably a method using distillation in terms of ease of operation and separability.

In purification step (2), dipropylene glycol and/or tripropylene glycol may be separated from the eighth liquid in one step, or alternatively tripropylene glycol may be separated after dipropylene glycol is separated.

When distillation is used as the method of performing the separation of purification step (2), distillation conditions are not particularly limited; the temperature within a distillation column is 0 to 300° C., preferably 10 to 250° C., the pressure within the distillation column is −0.1 to 1 MPa-G, preferably −0.09 to 0.1 MPa-G, and the number of plates of the distillation column is 1 to 100, preferably 10 to 50.

Step (K) is the step of removing at least a part of the alcohol compound contained in the seventh liquid from the seventh liquid to obtain a ninth liquid comprising the propylene glycol contained in the seventh liquid, optionally comprising the whole or a part of the water contained in the seventh liquid, and optionally comprising a part of the alcohol compound contained in the seventh liquid.

Step (K) may be performed by any method as long as the alcohol compound can be removed from the seventh liquid and step (K) can be practiced by partial condensation, distillation, extraction, adsorption, reaction, etc. In terms of ease of operation and separability, a method by partial condensation or distillation is preferred.

When distillation is used as the method of removing the alcohol compound of step (K), distillation conditions are not particularly limited; the temperature within a distillation column is 0 to 300° C., preferably 10 to 250° C., the pressure within the distillation column is −0.1 to 10 MPa-G, preferably −0.09 to 5 MPa-G, and the number of plates of the distillation column is 1 to 100, preferably 10 to 50.

In step (K), the alcohol compound may be removed from the seventh liquid in one step, or alternatively after the liquid containing unreacted water and propylene glycol is separated into water and propylene glycol, the alcohol compound may be removed from at least a part of the water separated or the propylene glycol separated.

As to step (K), the alcohol compound is preferably removed so that the concentration of the alcohol compound in total in the raw material liquid comprising propylene oxide and water for step (I) may become 2000 mmol/kg or less when the liquid obtained in step (K) has been recycled by step (L) described below as a component of the raw material liquid in step (I). The concentration of the alcohol compound in total in the raw material liquid for step (I) is more preferably 1000 mmol/kg or less; more preferably 400 mmol/kg or less, and most preferably 200 mmol/kg or less. If the concentration of the alcohol compound is 2000 mmol/kg or less, the selectivity to dipropylene glycol and/or tripropylene glycol improves more.

Examples of the alcohol compound to be removed in the present invention include methanol, ethanol, 1-propanol, 2-propanol, 1-butanol, 2-butanol, 2-methyl-1-propanol, 2-methyl-2-propanol, 1-pentanol, 3-methyl-1-butanol, 2,2-dimethyl-1-propanol, cyclopentanol, 1-hexanol, cyclohexanol, allyl alcohol, propylene glycol monopropyl ether, dipropylene glycol monopropyl ether, propylene glycol monoallyl ether, dipropylene glycol monoallyl ether, and hydroxyacetone; since especially allyl alcohol, 1-propanol, or 2-propanol will cause decrease in selectivity to dipropylene glycol and/or tripropylene glycol, allyl alcohol, 1-propanol, or 2-propanol is preferably removed.

Step (L) is the step of recycling at least a part of the ninth liquid to step (I) as a component of the raw material liquid.

The liquid to be recycled in step (L) is not restricted as long as it is a liquid resulting from removal of an alcohol compound from the seventh liquid, and examples thereof include a liquid obtained by removing an alcohol compound in one step from the liquid containing unreacted water and propylene glycol, a liquid obtained by separating a liquid containing unreacted water and propylene glycol into water and propylene glycol and then removing an alcohol compound from the water, and a liquid obtained by separating a liquid containing unreacted water and propylene glycol into water and propylene glycol and then removing an alcohol compound from the propylene glycol.

In the present invention, when unreacted propylene oxide is present in the reaction liquid obtained in the step (I), the unreacted propylene oxide may be collected and then reused by being recycled to step (I) as a component of the raw material liquid. The method of collecting the unreacted propylene oxide, which may be any method as long as it is a method by which the unreacted propylene oxide can be collected from the reaction liquid, is preferably a method using distillation from the viewpoint of ease of operation or separability.

When distillation is used as the method of collecting unreacted propylene oxide, distillation conditions are not particularly limited; the temperature within a distillation column is 0 to 300° C., preferably 10 to 250° C., the pressure within the distillation column is −0.1 to 20 MPa-G, preferably −0.09 to 10 MPa-G, and the number of plates of the distillation column is 1 to 100, preferably 10 to 50.

The third method of the present invention for producing dipropylene glycol and/or tripropylene glycol comprises steps (M), (N), (O), and (P) defined below, step (M): the step of reacting a raw material liquid comprising propylene oxide and water to obtain a reaction liquid comprising propylene glycol, dipropylene glycol and/or tripropylene glycol, and an alcohol compound excluding propylene glycol, dipropylene glycol, and tripropylene glycol, and optionally comprising unreacted water, step (N): the step of removing at least a part of the alcohol compound contained in the reaction liquid from the reaction liquid to obtain a tenth liquid comprising the propylene glycol and the dipropylene glycol and/or tripropylene glycol each contained in the reaction liquid and optionally comprising the water and/or apart of the alcohol compound each contained in the reaction liquid, step (O): the step of separating, from the tenth liquid, an eleventh liquid comprising the propylene glycol contained in the tenth liquid and optionally comprising the water and/or the alcohol compound each contained in the tenth liquid, and a twelfth liquid comprising the dipropylene glycol and/or tripropylene glycol contained in the tenth liquid and optionally comprising the alcohol compound contained in the tenth liquid, step (P): the step of recycling at least a part of the eleventh liquid to step (M) as a component of the raw material liquid.

Step (M) is the step of reacting a raw material liquid comprising propylene oxide and water to obtain a reaction liquid comprising propylene glycol, dipropylene glycol and/or tripropylene glycol, and an alcohol compound excluding propylene glycol, dipropylene glycol, and tripropylene glycol, and optionally comprising unreacted water.

In step (M), the propylene oxide and the water in the raw material liquid are consumed and dipropylene glycol and/or tripropylene glycol and an alcohol compound are generated. When the raw material liquid contains no propylene glycol, propylene glycol is generated in the reaction of step (M), whereas when the raw material liquid contains propylene glycol, propylene glycol is or is not generated in the reaction of step (M). In one embodiment, the raw material liquid comprises propylene glycol.

In step (M), the propylene oxide may be propylene oxide produced by any production method, and there can be used propylene oxide produced by dehydrochlorinating, with a basic compound, a mixture produced by making propylene react with an aqueous solution of chlorine, propylene oxide produced by making propylene react in the presence of a catalyst with ethylbenzene hydroperoxide produced by oxidizing ethylbenzene, propylene oxide produced by making propylene react in the presence of a catalyst with isopropylbenzene hydroperoxide produced by oxidizing isopropylbenzene, propylene oxide produced by making propylene react in the presence of a catalyst with tert-butyl hydroperoxide produced by oxidizing isobutane, and propylene oxide produced by making propylene react in the presence of a catalyst with hydrogen peroxide.

In step (M), distilled water, pure water, ion-exchanged water, steam condensate, etc. can be used as the water.

In step (M), the reaction is preferably performed in the presence of a catalyst in terms of improvement in selectivity. The catalyst to be used is not particularly restricted, and examples thereof include alkali metal hydroxides, such as lithium hydroxide, sodium hydroxide, potassium hydroxide, rubidium hydroxide, and cesium hydroxide, inorganic acids, such as hydrochloric acid, sulfuric acid, and phosphoric acid, ion exchange resin, zeolite, silica-alumina, amine compounds, and catalysts containing at least one element selected from the group consisting of vanadium, niobium, and tantalum. Among these catalysts, alkali metal hydroxides, such as lithium hydroxide, sodium hydroxide, potassium hydroxide, rubidium hydroxide, and cesium hydroxide, or catalysts containing at least one element selected from the group consisting of vanadium, niobium, and tantalum are preferable from the viewpoint of being high in selectivity to dipropylene glycol and/or tripropylene glycol. Examples of the catalysts containing at least one element selected from the group consisting of vanadium, niobium, and tantalum include vanadium pentoxide, vanadium dioxide, vanadium trioxide, niobium pentoxide, niobium dioxide, niobium monoxide, tantalum pentoxide, vanadic acid, niobic acid, and tantalic acid.

Such catalysts containing at least one element selected from the group consisting of vanadium, niobium, and tantalum may be used individually or in combination.

Such catalysts containing at least one element selected from the group consisting of vanadium, niobium, and tantalum may be used while having been mixed physically with a substantially inert solid. Examples of such a substantially inert solid include silica, alumina, titania, zirconia, ceria, activated carbon, graphite, magnesia, and calcia.

Examples of the reaction system of step (M) include a batch system using a tank reactor, a semi-continuous or continuous slurry method, and a continuous fixed bed method using a tubular reactor. As the tank reactor, a single-stage or multistage mixing tank is usually used. Examples of the tubular reactor include fixed bed reactors comprising a single unit or a plurality of units arranged in series, the unit or each of the units having a single tube or having a multitubular heat exchange structure having many tubes arranged in parallel.

The reaction temperature of step (M) is preferably 30 to 350° C., more preferably 50 to 300° C.

The reaction pressure applied when step (M) is carried out in a reactor, which may be any pressure under which the liquid within the reactor is in a liquid phase, is preferably normal pressure to 50 MPa-G, and more preferably 0.1 to 20 MPa-G.

In step (M), the amount of the water relative to the propylene oxide in the raw material liquid is preferably 0.05 to 100 mol, more preferably 0.1 to 50 mol, and even more preferably 0.2 to 10 mol per mol of propylene oxide.

Preferably, the raw material liquid in step (M) contains propylene glycol.

Step (N) is the step of removing at least a part of the alcohol compound contained in the reaction liquid from the reaction liquid to obtain a tenth liquid comprising the propylene glycol and the dipropylene glycol and/or tripropylene glycol each contained in the reaction liquid and optionally comprising the water and/or a part of the alcohol compound each contained in the reaction liquid.

Step (N) may be performed by any method as long as the alcohol compound can be removed from the reaction liquid and step (N) can be practiced by partial condensation, distillation, extraction, adsorption, reaction, etc. In terms of ease of operation and separability, a method by partial condensation or distillation is preferred.

When distillation is used as the method of removing the alcohol compound of step (N), distillation conditions are not particularly limited; the temperature within a distillation column is 0 to 300° C., preferably 10 to 250° C., the pressure within the distillation column is −0.1 to 10 MPa-G, preferably −0.09 to 5 MPa-G, and the number of plates of the distillation column is 1 to 100, preferably 10 to 50.

As to step (N), the alcohol compound is preferably removed so that the concentration of the alcohol compound in total in the raw material liquid comprising propylene oxide and water for step (M) may become 2000 mmol/kg or less when the liquid obtained in step (N) has been recycled by step (P) described below as a component of the raw material liquid in step (M). The concentration of the alcohol compound in total in the raw material liquid for step (M) is more preferably 1000 mmol/kg or less, more preferably 400 mmol/kg or less, and most preferably 200 mmol/kg or less. If the concentration of the alcohol compound is 2000 mmol/kg or less, the selectivity to dipropylene glycol and/or tripropylene glycol improves more.

Examples of the alcohol compound to be removed in the present invention include methanol, ethanol, 1-propanol, 2-propanol, 1-butanol, 2-butanol, 2-methyl-1-propanol, 2-methyl-2-propanol, 1-pentanol, 3-methyl-1-butanol, 2,2-dimethyl-1-propanol, cyclopentanol, 1-hexanol, cyclohexanol, allyl alcohol, propylene glycol monopropyl ether, dipropylene glycol monopropyl ether, propylene glycol monoallyl ether, dipropylene glycol monoallyl ether, and hydroxyacetone; since especially allyl alcohol, 1-propanol, or 2-propanol will cause decrease in selectivity to dipropylene glycol and/or tripropylene glycol, allyl alcohol, 1-propanol, or 2-propanol is preferably removed.

Step (O) is the step of separating, from the tenth liquid, an eleventh liquid comprising the propylene glycol contained in the tenth liquid and optionally comprising the water and/or the alcohol compound each contained in the tenth liquid, and a twelfth liquid comprising the dipropylene glycol and/or tripropylene glycol contained in the tenth liquid and optionally comprising the alcohol compound contained in the tenth liquid.

While the method of performing the separation of step (O) may be any method by which the tenth liquid can be separated into the eleventh liquid and the twelfth liquid, a method involving distillation is preferable in terms of ease of operation and separability.

When distillation is used as the method of performing the separation of step (O), distillation conditions are not particularly limited; the temperature within a distillation column is 0 to 300° C., preferably 10 to 250° C., the pressure within the distillation column is −0.1 to 5 MPa-G, preferably −0.09 to 1 MPa-G, and the number of plates of the distillation column is 1 to 100, preferably 10 to 50.

In the present invention, the step of separating dipropylene glycol and/or tripropylene glycol from the twelfth liquid (hereafter described as "purification step (3)") may be provided.

The method of performing the separation of purification step (3), which may be any method as long as it is a method by which dipropylene glycol and/or tripropylene glycol can be separated from the twelfth liquid, is preferably a method using distillation in terms of ease of operation and separability.

In purification step (3), dipropylene glycol and/or tripropylene glycol may be separated from the twelfth liquid in one step, or alternatively tripropylene glycol may be separated after dipropylene glycol is separated.

When distillation is used as the method of performing the separation of purification step (3), distillation conditions are not particularly limited; the temperature within a distillation column is 0 to 300° C., preferably 10 to 250° C., the pressure within the distillation column is −0.1 to 1 MPa-G, preferably −0.09 to 0.1 MPa-G, and the number of plates of the distillation column is 1 to 100, preferably 10 to 50.

Step (P) is the step of recycling at least a part of the eleventh liquid to step (M) as a component of the raw material liquid.

In the present invention, when unreacted propylene oxide is present in the reaction liquid obtained in the step (M), the unreacted propylene oxide may be collected and then reused by being recycled to step (M). The method of collecting the unreacted propylene oxide, which may be any method as long as it is a method by which the unreacted propylene oxide can be collected from the reaction liquid, is preferably a method using distillation from the viewpoint of ease of operation or separability.

When distillation is used as the method of collecting unreacted propylene oxide, distillation conditions are not particularly limited; the temperature within a distillation column is 0 to 300° C., preferably 10 to 250° C., the pressure within the distillation column is 0.1 to 20 MPa-G, preferably −0.09 to 10 MPa-G, and the number of plates of the distillation column is 1 to 100, preferably 10 to 50.

EXAMPLES

The present invention is described in detail below with reference to examples. For distillation calculation in Examples 1 and 3 was used software marketed under the trademark of ASPEN PLUS (supplied by Aspen Technology, Inc., Cambridge, Mass.). Conversion and selectivity in examples were calculated using the following formulae.

$$\text{Selectivity to dipropylene glycol} = \{\text{the number of moles of dipropylene glycol generated} \times 2/(\text{the number of moles of propylene oxide consumed})\} \times 100(\%)$$

$$\text{Selectivity to tripropylene glycol} = \{\text{the number of moles of tripropylene glycol generated} \times 3/(\text{the number of moles of propylene oxide consumed})\} \times 100(\%)$$

Reference Example 1

Into a reaction tube having an inner diameter of 10 mm within which a sheath tube having an outside diameter of 3 mm had been inserted was filled 46 g of a niobium pentoxide catalyst. Through this reaction tube was made to pass at an inlet temperature of 110° C., an outlet temperature of 230° C. and a pressure of 1 MPa-G a liquid prepared by mixing 24 parts by weight of propylene oxide, 16 parts by weight of water, 36 parts by weight of propylene glycol, 21 parts by weight of dipropylene glycol, and 4 parts by weight of tripropylene glycol at a rate of 125 g/h for 8 hours, so that 1000 g of a reaction liquid A-0 was obtained. In reaction liquid A-0 was contained 12 parts by weight of water, 36 parts by weight of propylene glycol, 44 parts by weight of dipropylene glycols, 7 parts by weight of tripropylene glycol, 0.06 parts by weight of allyl alcohol, and 0.005 parts by weight of 1-propanol, whereas propylene oxide and 2-propanol were contained, if any, in amounts not more than their lower detection limits.

Example 1

For the reaction liquid A-0 obtained in Reference Example 1, steps (B) and (C), step (D), steps (E) and (F), and step (A) are performed.

Steps (B) and (C): 510 g of the reaction liquid A-0 is supplied to the tenth plate, counted from the top, of a distillation column having 20 plates as illustrated in (FIG. 1) at a rate of 64 g/h and a second liquid B-1 containing propylene glycol, dipropylene glycol and tripropylene glycol is separated from the column bottom at a flow rate of 56 g/h, so that a first liquid containing water and an alcohol compound is obtained. In addition, the first liquid is subjected for 8 hours to operations in which a liquid C-1 containing the alcohol compound is removed from the column top at a flow rate of 1 g/h and a third liquid D-1 containing water with removal of part of the alcohol compound is obtained at the second plate of the distillation column (i.e., a side-cut part) at a flow rate of 7 g/h. Thus, 446 g of the second liquid B-1, 11 g of the liquid C-1 containing the alcohol compound, and 53 g of the third liquid D-1 are obtained. In the liquid C-1 containing the alcohol compound are contained 68% of the allyl alcohol to be supplied and 79% of the 1-propanol to be supplied, whereas in the liquid D-1 which contains unreacted water and from which the alcohol compound is to be removed, 32% of the allyl alcohol to be supplied and 21% of the 1-propanol to be supplied are contained.

The distillation conditions are a pressure of −0.04 MPa-G, a column bottom temperature of 199° C., a column top temperature of 88° C., and a side-cut part temperature of 88° C.

Step (D): operations of supplying the second liquid B-1 obtained in steps (B) and (C) to the tenth plate, counted from the top, of a distillation column having 20 plates at a rate of 56 g/h, separating a fifth liquid E-1 containing dipropylene glycol and tripropylene glycol from the column bottom at a flow rate of 33 g/h, and distilling off a fourth liquid F-1 containing propylene glycol from the column top at a flow rate of 23 g/h are performed for 8 hours. Thus, 265 g of the fifth liquid E-1 and 181 g of the fourth liquid F-1 are obtained.

The distillation conditions are a pressure of −0.09 MPa-G, a column bottom temperature of 179° C., and a column top temperature of 132° C.

Steps (E) and (F): 232 g of propylene oxide, 44 g of water, 490 of reaction liquid A-0, 53 g of the third liquid D-1 obtained in steps (B) and (C), and 181 g of the fourth liquid F-1 obtained in step (D) are mixed to obtain 1000 g of a raw material liquid G-1.

Step (A): the raw material liquid G-1 is made to pass through a reaction tube having an inner diameter of 10 mm within which a sheath tube having an outside diameter of 3 mm filled with 46 g of a niobium pentoxide catalyst has been inserted, at a rate of 125 g/h for 8 hours at an inlet temperature of 110° C., an outlet temperature of 230° C., and a pressure of 1 MPa-G, so that 1000 g of a reaction liquid A-1 is obtained.

For the reaction liquid A-1, the operations of steps (B) and (C), step (D), steps (E) and (F), and step (A) are performed. When performing the operations of steps (B) and (C), step (D), and steps (E) and (F), the operations are performed with A-0, B-1, C-1, D-1, E-1, F-1, and G-1 changed to A-1, B-2, C-2, D-2, E-2, F-2, and G-2, respectively, and when performing the operation of step (A), the operation is performed with G-1 and A-1 changed to G-2 and A-2, respectively.

Similarly, the operations of steps (B) and (C), step (D), steps (E) and (F), and step (A) are performed for a reaction liquid A-(k−1) (k is an integer of 3 or more). When performing the operations of steps (B) and (C), step (D), and steps (E) and (F), the operations are performed with A-0, B-1, C-1, D-1, E-1, F-1, and G-1 changed to A-(k−1), B-k, C-k, D-k, E-k, F-k, and G-k, respectively, and when performing the operation of step (A), the operation is performed with G-1 and A-1 changed to G-k and A-k, respectively.

A series of the operations of steps (B) and (C) step (D) steps (E) and (F), and step (A) is performed 268 times. Then, the operations of steps (B) and (C), step (D), and steps (E) and (F) are performed to obtain a raw material liquid G-269. In the raw material liquid G-269, 0.11 parts by weight of allyl alcohol and 0.01 parts by weight of 1-propanol are contained, whereas 2-propanol is contained, if any, in an amount not more than its lower detection limit (the total concentration of allyl alcohol, 1-propanol and 2-propanol in the raw material liquid: 21 mmol/kg).

23 parts by weight of propylene oxide, 16 parts by weight of water, 36 parts by weight of propylene glycol, 21 parts by weight of dipropylene glycol, 4 parts by weight of tripropylene glycol, 0.11 parts by weight of allyl alcohol, and 0.01 parts by weight of 1-propanol were mixed to obtain a model raw material liquid A having the same alcohol compound concentration as the raw material liquid G-269.

The model raw material liquid A was made to pass through a reaction tube having an inner diameter of 10 mm within which a sheath tube having an outside diameter of 3 mm filled with 14 g of a niobium pentoxide catalyst has been inserted, at a rate of 34 g/h at an average internal temperature of 149° C. and a pressure of 1 MPa-G. The selectivity to dipropylene glycol was 79% and the selectivity to tripropylene glycol was 15%.

Comparative Example 1

For the reaction liquid A-0 obtained in Reference Example 1, steps (B)', (D)', (E)' and (A)' each described below are performed instead of steps (B) and (C), step (D), steps (E) and (F), and step (A).

Figure 2:
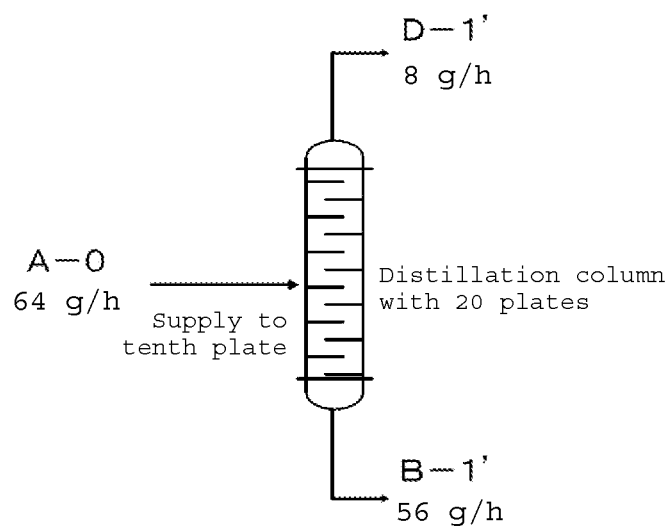
FIG. 2 is a diagram illustrating step (B)' of Comparative Example 1.

Step (B)': operations of supplying 510 g of the reaction liquid A-0 to the tenth plate, counted from the top, of a distillation column having 20 plates as illustrated in (FIG. 2) at a rate of 64 g/h, separating a liquid B-1' containing propylene glycol, dipropylene glycol and tripropylene glycol from the column bottom at a flow rate of 56 g/h, and obtaining a liquid D-1' containing water and an alcohol compound from the column top at a flow rate of 8 g/h are performed for 8 hours. Thus, 446 g of the liquid B-1' containing propylene glycol, dipropylene glycol and tripropylene glycol, and 64 g of the liquid D-1' containing water and the alcohol compound are obtained. In the liquid D-1' containing water and the alcohol compound, 100% of the allyl alcohol supplied and 100% of the 1-propanol supplied are contained.

The distillation conditions are a pressure of −0.04 MPa-G, a column bottom temperature of 199° C., and a column top temperature of 88° C.

Step (D)': operations of supplying 446 g of the liquid B-1' obtained in step (B)' and containing propylene glycol, dipropylene glycol and tripropylene glycol to the tenth plate counted from the top of a distillation column having 20 plates at a rate of 56 g/h, separating a liquid E-1' containing dipropylene glycol and tripropylene glycol from the column bottom at a flow rate of 33 g/h, and distilling off a liquid F-1' containing propylene glycol from the column top at a flow rate of 23 g/h are performed for 8 hours. Thus, 265 g of the liquid E-1' containing dipropylene glycol and tripropylene glycol and 181 g of a liquid F'-1 containing propylene glycol are obtained.

The distillation conditions are a pressure of −0.09 MPa-G, a column bottom temperature of 179° C., and a column top temperature of 132° C.

Step (E)': 232 g of propylene oxide, 33 g of water, 490 g of the reaction liquid A-0, 64 g of the liquid D-1' obtained in step (B)' and containing water and the alcohol compound, and 181 g of the liquid F-1' obtained in step (D) and containing propylene glycol are mixed to obtain 1000 g of a raw material liquid G-1'.

Step (A)': the raw material liquid G-1' is made to pass through a reaction tube having an inner diameter of 10 mm within which a sheath tube having an outer diameter of 3 mm filled with 46 g of a niobium pentoxide catalyst has been inserted, at a rate of 125 g/h for 8 hours at an inlet temperature of 110° C., an outlet temperature of 230° C., and a pressure of 1 MPa-G, so that 1000 g of a reaction liquid A-1' is obtained.

For the reaction liquid A-1', the operations of step (B)', step (D)', step (E)' and step (A)' are performed. When performing the operations of step (B)', step (D)', and step (E)', the operations are performed with A-0, B-1', D-1', E-1', F-1', and G-1' changed to A-1', B-2', D-2', E-2', F-2', and G-2', respectively, and when performing the operation of step (A)', the operation is performed with G-1' and A-1' changed to G-2' and A-2', respectively.

Similarly, the operations of step (B)', step (D)', step (E)', and step (A)' are performed for a reaction liquid A-(k−1) (k is an integer of 3 or more). When performing the operations of step (B)', step (D)', and step (E)', the operations are performed with A-0, B-1', D-1', E-1', F-1', and G-1' changed to A-(k−1)', B-k', D-k', E-k', F-k', and G-k', respectively, and when performing the operation of step (A)', the operation is performed with G-1' and A-1' changed to G-k' and A-k', respectively.

A series of the operations of step (B)', step (D)', step (E)' and step (A)' is repeated 268 times. Then, the operations of step (B)', step (D)' and step (E)' are performed to obtain a raw material liquid G-269'. In the raw material liquid G-269', 16 parts by weight of allyl alcohol and 1 part by weight of 1-propanol are contained, whereas 2-propanol is contained, if any, in an amount not more than its lower detection limit (the total concentration of allyl alcohol, 1-propanol and 2-propanol in the raw material liquid: 2924 mmol/kg).

23 parts by weight of propylene oxide, 12 parts by weight of water, 28 parts by weight of propylene glycol, 17 parts by weight of dipropylene glycol, 3 parts by weight of tripropylene glycol, 16 parts by weight of allyl alcohol, and 1 part by weight of 1-propanol were mixed to obtain a model raw material liquid B having the same alcohol compound concentration as the raw material liquid G-269'.

The model raw material liquid B was made to pass through a reaction tube having an inner diameter of 10 mm within which a sheath tube having an outside diameter of 3 mm filled with 14 g of a niobium pentoxide catalyst has been inserted, at a rate of 34 g/h at an average internal temperature of 149° C. and a pressure of 1 MPa-G. The selectivity to dipropylene glycol was 78% and the selectivity to tripropylene glycol was 12%.

Example 2

Steps (J) and (K), step (L), and step (I) were performed for the reaction liquid A-0 obtained in Reference Example 1.

Figure 3:
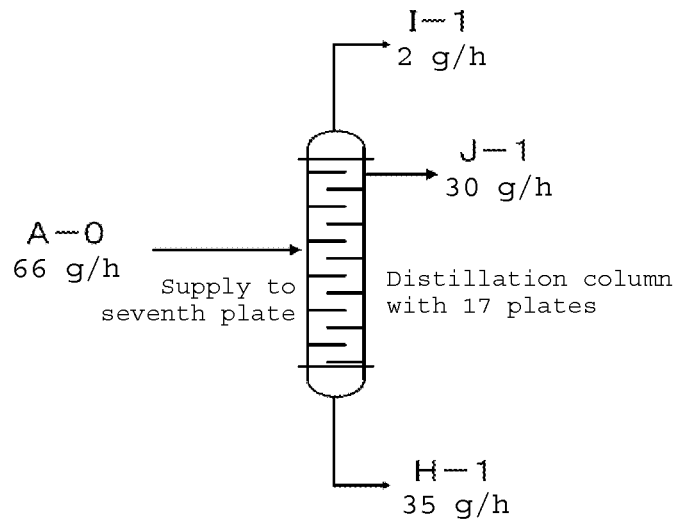
FIG. 3 is a diagram illustrating steps (J) and (K) of Example 2.

Steps (J) and (K): 530 g of the reaction liquid A-0 was supplied to the seventh plate, counted from the top, of a distillation column having 17 plates as illustrated in (FIG. 3) at a rate of 66 g/h and an eighth liquid H-1 containing dipropylene glycol and tripropylene glycol was separated from the column bottom at a flow rate of 35 g/h, so that a seventh liquid containing water, an alcohol compound and propylene glycol is obtained. In addition, the seventh liquid was subjected for 8 hours to operations in which a liquid I-1 containing the alcohol compound was removed from the column top at a flow rate of 2 g/h and a ninth liquid J-1 containing water and propylene glycol with removal of part of the alcohol compound was distilled off at the second plate of the distillation column (i.e., a side-cut part) at a flow rate of 30 g/h. Thus, 276 g of the eighth liquid H-1, 15 g of the liquid I-1 containing the alcohol compound, and 239 g of the ninth liquid J-1 were obtained. In the liquid I-1 containing the alcohol compound, 84% of the allyl alcohol supplied and 88% of the 1-propanol supplied were contained, whereas in the ninth liquid J-1, 20 parts by weight of water and 79 parts by weight of propylene glycol were contained and further 16% of the allyl alcohol supplied and 12% by weight of the 1-propanol supplied were contained.

The distillation conditions were a pressure of −0.09 MPa-G, a column bottom temperature of 174° C., a side-cut part temperature of 123° C., and a column bottom temperature of 46° C.

Step (L): 240 g of propylene oxide, 51 g of water, 470 g of the reaction liquid A-0, and 239 g of the ninth liquid J-1 obtained in steps (J) and (K) were mixed to obtain 1000 g of a raw material liquid K-1.

Step (I): the raw material liquid K-1 was made to pass through a reaction tube having an inner diameter of 10 mm within which a sheath tube having an outside diameter of 3 mm filled with 46 g of a niobium pentoxide catalyst had been inserted, at a rate of 125 g/h for 8 hours at an inlet temperature of 110° C., an outlet temperature of 230° C., and a pressure of 1 MPa-G, so that 1000 g of a reaction liquid L-1 was obtained.

For the reaction liquid L-1, the operations of steps (J) and (K), step (L), and step (I) were performed. When performing the operations of steps (J) and (K) and step (L), the operations were performed with A-0, H-1, I-1, J-1, and K-1 changed to L-1, H-2, I-2, J-2, and K-2, respectively, and when performing the operation of step (I), the operation was performed with K-1 and L-1 changed to K-2 and L-2, respectively.

Similarly, the operations of steps (J) and (K), step (L), and step (I) were performed for a reaction liquid L-(k−1) (k is an integer of 3 or more). When performing the operations of steps (J) and (K), and step (L), the operations were performed with A-0, H-1, I-1, J-1, and K-1 changed to L-(k−1), H-k, I-k, J-k, and K-k, respectively, and when performing the operation of step (I), the operation was performed with K-1 and L-1 changed to K-k and L-k, respectively.

A series of the operations of steps (J) and (K), step (L), and step (I) was performed 268 times. Then, the operations of steps (J) and (K), and step (L) were performed to obtain a raw material liquid K-269. In the raw material liquid G-269, 23 parts by weight of propylene oxide, 16 parts by weight of water, 39 parts by weight of propylene glycol, 19 parts by weight of dipropylene glycol, 3 parts by weight of tripropylene glycol, 0.05 parts by weight of allyl alcohol, and 0.01 parts by weight of 1-propanol were contained, whereas the 2-propanol concentration was not more than the lower detection limit (the total concentration of allyl alcohol, 1-propanol and 2-propanol in the raw material liquid: 10 mmol/kg).

The raw material liquid K-269 was made to pass through a reaction tube having an inner diameter of 10 mm within which a sheath tube having an outside diameter of 3 mm filled with 46 g of a niobium pentoxide catalyst had been inserted, at a rate of 125 g/h at an inlet temperature of 110° C., an outlet temperature of 230° C., and a pressure of 1 MPa-G. The selectivity to dipropylene glycol was 83% and the selectivity to tripropylene glycol was 15%.

Comparative Example 2

For the reaction liquid A-0 obtained in Reference Example 1, step (J)', step (L)', and step (I)' each described below are performed instead of steps (J) and (K), step (L), and step (I).

Figure 4:
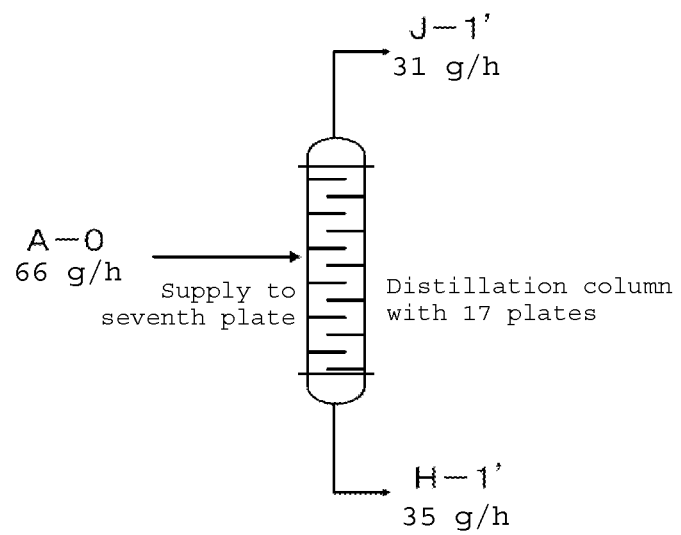
FIG. 4 is a diagram illustrating step (J)' of Comparative Example 2.

Step (J)': operations of supplying 530 g of the reaction liquid A-0 to the seventh plate, counted from the top, of a distillation column having 17 plates as illustrated in (FIG. 4) at a rate of 66 g/h, separating a liquid H-1' containing dipropylene glycol and tripropylene glycol from the column bottom at a flow rate of 35 g/h, and distilling off a liquid J-1' containing water, propylene glycol and the alcohol compound from the column top at a flow rate of 31 g/h are performed for 8 hours. Thus, 276 g of a liquid H-1' containing dipropylene glycol and tripropylene glycol and 254 g of a liquid J'-1 containing water, propylene glycol and the alcohol compound are obtained. In the liquid J-1' containing water, propylene glycol and the alcohol compound, 100% of the allyl alcohol supplied and 100% of the 1-propanol supplied are contained.

The distillation conditions are a pressure of −0.09 MPa-G, a column bottom temperature of 174° C., and a column top temperature of 123° C.

Step (L)': 240 g of propylene oxide, 36 g of water, 470 g of the reaction liquid A-0, and 254 g of the liquid J-1' obtained in step (J)' and containing water, propylene glycol and the alcohol compound are mixed to obtain a raw material liquid K-1'.

Step (I)': the raw material liquid K-1' is made to pass through a reaction tube having an inner diameter of 10 mm within which a sheath tube having an outside diameter of 3 mm filled with 46 g of a niobium pentoxide catalyst has been inserted, at a rate of 125 g/h for 8 hours at an inlet temperature of 110° C., an outlet temperature of 230° C., and a pressure of 1 MPa-G, so that 1000 g of a reaction liquid L-1' was obtained.

The operations of step (J)', step (L), and step (I)' are performed for the reaction liquid L-1'. When performing the operations of step (J)' and step (L)', the operations are performed with A-0, H-1', J-1', and K-1' changed to L-1', H-2', J-2', and K-2', respectively, and when performing the operation of step (I)', the operation is performed with K-1' and L-1' changed to K-2' and L-2', respectively.

Similarly, the operations of step (J)', step (L)', and step (I)' are performed for a reaction liquid L-(k−1)' (k is an integer of 3 or more). When performing the operations of step (J)' and step (L)', the operations are performed with A-0, H-1', J-1', and K-1' changed to L-(k−1)', H-k', J-k', and K-k', respectively, and when performing the operation of step (I)', the operation is performed with K-1' and L-1' changed to K-k' and L-k', respectively.

A series of the operations of step (J)', step (L)', and step (I)' is performed 268 times. Then, the operations of step (J)' and step (L)' are performed to obtain a raw material liquid K-269'. In the raw material liquid K-269', 16 parts by weight of allyl alcohol and 1 part by weight of 1-propanol are contained, whereas 2-propanol is contained, if any, in an amount not more than its lower detection limit (the total concentration of allyl alcohol, 1-propanol and 2-propanol in the raw material liquid: 2924 mmol/kg).

22 parts by weight of propylene oxide, 12 parts by weight of water, 33 parts by weight of propylene glycol, 13 parts by weight of dipropylene glycol, 2 parts by weight of tripropylene glycol, 16 parts by weight of allyl alcohol, and 1 part by weight of 1-propanol were mixed to obtain a model raw material liquid C having the same alcohol compound concentration as the raw material liquid K-269'.

The model raw material liquid C was made to pass through a reaction tube having an inner diameter of 10 mm within which a sheath tube having an outside diameter of 3 mm filled with 46 g of a niobium oxide catalyst had been inserted, at a rate of 125 g/h at an inlet temperature of 110° C., an outlet temperature of 230° C., and a pressure of 1 MPa-G. The selectivity to dipropylene glycol was 75% and the selectivity to tripropylene glycol was 11%.

Reference Example 2

Into a 200 mL autoclave were introduced 36 g of propylene oxide, 71 g of water, 43 g of propylene glycol, and 0.8 g of sodium hydroxide, and then the inside of the autoclave was flushed fully with nitrogen gas. Heat was applied so as to adjust the liquid temperature within the autoclave to 100° C. and a reaction was performed for 60 minutes under stirring to obtain 151 g of a reaction liquid M-0. In the reaction liquid M-0, 0.02 parts by weight of propylene oxide, 45 parts by weight of water, 29 parts by weight of propylene glycol, 22 parts by weight of dipropylene glycol, 4 parts by weight of tripropylene glycol, and 0.0007 parts by weight of allyl alcohol were contained, and the contents of 1-propanol and 2-propanol were their lower detection limits or less.

Example 3

For the reaction liquid M-0 obtained in Reference Example 2, the operations of step (N), step (O), step (P), and step (M) are performed.

Step (N): operations of supplying 151 g of the obtained reaction liquid M-0 to the tenth plate, counted from the top, of a distillation column having 20 plates at a rate of 50 g/h, obtaining a liquid N-1 containing propylene glycol, dipropylene glycol and tripropylene glycol from the column bottom at a flow rate of 28 g/h, and removing a liquid O-1 containing water and an alcohol compound from the column top at a flow rate of 22 g/h are performed for 3 hours. Thus, 84 g of the tenth liquid N-1 containing propylene glycol, dipropylene glycol and tripropylene glycol with removal of the alcohol compound, and 67 g of the liquid O-1 containing water and the alcohol compound are obtained. In the liquid O-1 containing water and an alcohol compound, 100% of the allyl alcohol supplied is contained, whereas substantially no allyl alcohol is contained in the tenth liquid N-1.

The distillation conditions are a pressure of −0.04 MPa-G, a column bottom temperature of 196° C., and a column top temperature of 86° C.

Step (O): operations of supplying 84 g of the tenth liquid N-1 obtained in step (N) to the tenth plate, counted from the top, of a distillation column having 20 plates at a rate of 28 g/h, separating a twelfth liquid P-1 containing dipropylene glycol and tripropylene glycol from the column bottom at a flow rate of 14 g/h, and distilling off an eleventh liquid Q-1 containing propylene glycol from the column top at a flow rate of 14 g/h are performed for 3 hours. Thus, 41 g of the twelfth liquid P-1 and 43 g of the eleventh liquid Q-1 are obtained.

The distillation conditions are a pressure of −0.09 MPa-G, a column bottom temperature of 179° C., and a column top temperature of 132° C.

Step (P): 36 g of propylene oxide, 71 g of water, and 43 g of the eleventh liquid Q-1 obtained in step (O) are mixed to obtain 150 g of a raw material liquid R-1.

Step (M): into a 200 mL autoclave were introduced 150 g of the raw material liquid R-1 obtained in step (P) and 0.8 g of sodium hydroxide, and then the inside of the autoclave was flushed fully with nitrogen gas. Heat is applied so as to adjust the liquid temperature within the autoclave to 100° C. and a reaction was performed for 60 minutes under stirring to obtain 151 g of a reaction liquid M-1.

For the reaction liquid M-1, the operations of step (N), step (O), step (P), and step (M) are performed. When performing the operations of step (N), step (O), and step (P), the operations are performed with M-0, N-1, O-1, P-1, Q-1, and R-1 changed to M-1, N-2, O-2, P-2, Q-2, and R-2, respectively, and when performing the operation of step (M), the operation is performed with R-1 and M-1 changed to R-2 and M-2, respectively.

Similarly, the operations of steps (N) and (O), step (P), and step (M) are performed for a reaction liquid M-(k−1) (k is an integer of 3 or more). When performing the operations of step (N), step (O), and step (P), the operations are performed with M-0, N-1, O-1, P-1, Q-1, and R-1 changed to M-(k−1), N-k, O-k, P-k, Q-k, and R-k, respectively, and when performing the operation of step (M), the operation is performed with R-1 and M-1 changed to R-k and M-k, respectively.

A series of the operations of step (N), step (O), step (P), and step (M) is performed 21213 times. Then, the operations of step (N), step (O), and step (P) are performed to obtain a raw material liquid R-21214. The allyl alcohol concentration, the 1-propanol concentration, and the 2-propanol concentration of the raw material liquid R-21214 are not more than lower detection limits (the total concentration of allyl alcohol, 1-propanol and 2-propanol in the raw material liquid: 0 mmol/kg).

36 g of propylene oxide, 71 g of water, and 43 g of propylene glycol were mixed to obtain a model raw material liquid D having the same alcohol compound concentration as the raw material liquid R-21214.

Into a 200 mL autoclave were introduced the model raw material liquid D and 0.8 g of sodium hydroxide, and then the inside of the autoclave was flushed fully with nitrogen gas. Heat was applied so as to adjust the liquid temperature within the autoclave to 100° C. and reaction was performed for 60 minutes under stirring, affording a reaction liquid. The selectivity to dipropylene glycol was 79% and the selectivity to tripropylene glycol was 15%.

Comparative Example 3

For the reaction liquid M-0 obtained in Reference Example 2, step (N)', step (P)', and step (M)' each described below are performed instead of step (N), step (O), step (P), and step (M).

Step (N)': operations of supplying 151 g of the obtained reaction liquid M-0 to the tenth plate, counted from the top, of a distillation column having 20 plates at a rate of 50 g/h, separating a liquid P-1' containing dipropylene glycol and tripropylene glycol from the column bottom at a flow rate of 14 g/h, and distilling off a liquid Q-1' containing water, propylene glycol and the alcohol compound from the column top at a flow rate of 37 g/h are performed for 3 hours. Thus, 41 g of the liquid P-1' containing dipropylene glycol and tripropylene glycol and 110 g of the liquid Q-1' containing water, propylene glycol and the alcohol compound are obtained. In the liquid Q-1' containing water, propylene glycol and the alcohol compound, 100% of the allyl alcohol supplied is contained.

The distillation conditions are a pressure of −0.09 MPa-G, a column bottom temperature of 179° C., and a column top temperature of 50° C.

Step (P)': 36 g of propylene oxide, 4 g of water, and 110 g of a liquid Q-1' containing water, propylene glycol, and the alcohol compound and obtained in step (N)' are mixed to obtain 150 g of a raw material liquid R-1'.

Step (M)': into a 200 mL autoclave were introduced 150 g of the raw material liquid R-1' obtained in step (P)' and 0.8 g of sodium hydroxide, and then the inside of the autoclave was flushed fully with nitrogen gas. Heat is applied so as to adjust the liquid temperature within the autoclave to 100° C. and a reaction was performed for 60 minutes under stirring to obtain 151 g of a reaction liquid M-1'.

Operations of step (N)', step (P)', and step (M)' are performed for the reaction liquid M-1'. When performing the operations of step (N)', step (O)', and step (P)', the operations are performed with M-0, P-1', Q-1', and R-1' changed to M-1', P-2', Q-2', and R-2', respectively, and when performing the operation of step (M)', the operation is performed with R-1' and M-1' changed to R-2' and M-2', respectively.

Similarly, the operations of step (N)', step (P)', and step (M)' are performed for a reaction liquid M-(k−1) (k is an integer of 3 or more). When performing the operations of step (N)', step (O)', and step (P)', the operations are performed with M-0, P-1', Q-1', and R-1' changed to M-(k−1)', P-k', Q-k', and R-k', respectively, and when performing the operation of step (M)', the operation is performed with R-1' and M-1' changed to R-k' and M-k', respectively.

A series of the operations of step (N)', step (P)', and step (M)' is performed 21213 times. Then, the operations of step (N)' and step (P)' are performed to obtain a raw material liquid R-21214'. In the raw material liquid R-21214' is contained 15 parts by weight of allyl alcohol, and the 1-propanol concentration and the 2-propanol concentration are not more than lower detection limits (the total concentration of allyl alcohol, 1-propanol and 2-propanol in the raw material liquid: 2548 mmol/kg).

36 g of propylene oxide, 58 g of water, 34 g of propylene glycol, and 22 g of allyl alcohol were mixed to obtain a model raw material liquid E having the same alcohol compound concentration as the raw material liquid R-21214'.

Into a 200 mL autoclave were introduced the model raw material liquid E and 0.8 g of sodium hydroxide, and then the inside of the autoclave was flushed fully with nitrogen gas. Heat was applied so as to adjust the liquid temperature within the autoclave to 100° C. and reaction was performed for 60 minutes under stirring. The selectivity to dipropylene glycol was 56% and the selectivity to tripropylene glycol was 9%.

The invention claimed is:

1. A method for producing dipropylene glycol and/or tripropylene glycol, the method comprising steps (A), (B), (C), (D), and (E):

step (A): reacting a raw material liquid comprising propylene oxide and water to obtain a reaction liquid comprising unreacted water, propylene glycol, dipropylene glycol and/or tripropylene glycol, and an alcohol compound excluding propylene glycol, dipropylene glycol, and tripropylene glycol, step (B): separating from the reaction liquid a first liquid comprising the water and at least a portion of the alcohol compound contained in the reaction liquid, and a second liquid comprising the propylene glycol and the dipropylene glycol and/or tripropylene glycol contained in the reaction liquid and optionally comprising the remaining portion of the alcohol compound contained in the reaction liquid, step (C): removing at least a part of the alcohol compound contained in the first liquid from the first liquid to obtain a third liquid comprising the water contained in the first liquid and optionally a part of the alcohol compound contained in the first liquid, step (D): separating from the second liquid a fourth liquid comprising the propylene glycol contained in the second liquid and optionally comprising a first portion of the alcohol compound contained in the second liquid, and a fifth liquid comprising the dipropylene glycol and/or tripropylene glycol contained in the second liquid and optionally comprising a second portion of the alcohol compound contained in the second liquid, step (E): recycling at least a part of the third liquid to step (A) as a component of the raw material liquid.

2. The method according to claim 1, further comprising step (F):

step (F): recycling at least a part of the fourth liquid to step (A) as a component of the raw material liquid.

3. The method according to claim 1, further comprising steps (G) and (H):
- step (G): removing at least a part of the alcohol compound contained in the fourth liquid if present from the fourth liquid to obtain a sixth liquid comprising the propylene glycol contained in the fourth liquid and optionally comprising a part of the alcohol compound contained in the fourth liquid,
- step (H): recycling at least a part of the sixth liquid to step (A) as a component of the raw material liquid.

4. The method according to claim 1, wherein the alcohol compound is at least one species selected from allyl alcohol, 1-propanol, and 2-propanol.

5. A method for producing dipropylene glycol and/or tripropylene glycol, the method comprising steps (A), (B), (C), and (D):
- step (A): reacting a raw material liquid comprising propylene oxide and water to obtain a reaction liquid comprising unreacted water, propylene glycol, dipropylene glycol and/or tripropylene glycol, and an alcohol compound excluding propylene glycol, dipropylene glycol, and tripropylene glycol,
- step (B): separating from the reaction liquid a first liquid comprising the water, at least a portion of the alcohol compound, and the propylene glycol contained in the reaction liquid, and a second liquid comprising the dipropylene glycol and/or tripropylene glycol contained in the reaction liquid and optionally comprising the remaining portion of the alcohol compound contained in the reaction liquid,
- step (C): removing at least a part of the alcohol compound contained in the first liquid from the first liquid to obtain a third liquid comprising the propylene glycol contained in the first liquid, optionally at least a part of the water contained in the first liquid, and optionally a part of the alcohol compound contained in the first liquid,
- step (D): recycling at least a part of the third liquid to step (A) as a component of the raw material liquid.

6. The method according to claim 5, wherein the alcohol compound is at least one species selected from allyl alcohol, 1-propanol, and 2-propanol.

7. A method for producing dipropylene glycol and/or tripropylene glycol, the method comprising steps (A), (B), (C), and (D):
- step (A): reacting a raw material liquid comprising propylene oxide and water to obtain a reaction liquid comprising propylene glycol, dipropylene glycol and/or tripropylene glycol, and an alcohol compound excluding propylene glycol, dipropylene glycol, and tripropylene glycol, and optionally comprising unreacted water,
- step (B): removing at least a part of the alcohol compound contained in the reaction liquid from the reaction liquid to obtain a first liquid comprising the propylene glycol and the dipropylene glycol and/or tripropylene glycol contained in the reaction liquid and optionally comprising the water and/or a part of the alcohol compound contained in the reaction liquid,
- step (C): separating from the first liquid a second liquid comprising the propylene glycol contained in the first liquid and optionally a first portion of the water and/or the alcohol compound each contained in the first liquid, and a third liquid comprising the dipropylene glycol and/or tripropylene glycol contained in the first liquid and optionally a second portion of the alcohol compound contained in the first liquid,
- step (D): recycling at least a part of the second liquid to step (A) as a component of the raw material liquid.

8. The method according to claim 7, wherein the alcohol compound is at least one species selected from allyl alcohol, 1-propanol, and 2-propanol.

9. The method according to claim 2, wherein the alcohol compound is at least one species selected from allyl alcohol, 1-propanol, and 2-propanol.

10. The method according to claim 3, wherein the alcohol compound is at least one species selected from allyl alcohol, 1-propanol, and 2-propanol.

* * * * *